United States Patent
Chuang et al.

(10) Patent No.: US 10,273,393 B2
(45) Date of Patent: Apr. 30, 2019

(54) METHOD OF PRODUCING ALKOXYLENE DERIVATIVE AND APPLICATION THEREOF

(71) Applicant: SINO-JAPAN CHEMICAL CO., LTD., Taipei (TW)

(72) Inventors: Chung-Che Chuang, Kaohsiung (TW); Ya-Hui Lin, Kaohsiung (TW)

(73) Assignee: SINO-JAPAN CHEMICAL CO., LTD., Taipei (TW)

( * ) Notice: Subject to any disclaimer, the term of this patent is extended or adjusted under 35 U.S.C. 154(b) by 101 days.

(21) Appl. No.: 15/262,017

(22) Filed: Sep. 12, 2016

(65) Prior Publication Data

US 2017/0114261 A1 Apr. 27, 2017

(30) Foreign Application Priority Data

Oct. 23, 2015 (TW) .............................. 104134917 A

(51) Int. Cl.
| | | |
|---|---|---|
| *C09K 3/18* | (2006.01) | |
| *C07C 41/02* | (2006.01) | |
| *C07C 43/15* | (2006.01) | |
| *C09D 133/14* | (2006.01) | |
| *C09K 3/16* | (2006.01) | |
| *C07C 41/03* | (2006.01) | |
| *C07F 9/00* | (2006.01) | |
| *C08G 65/00* | (2006.01) | |
| *C09D 133/06* | (2006.01) | |
| *C07C 303/34* | (2006.01) | |
| *C07C 307/02* | (2006.01) | |

(52) U.S. Cl.
CPC .............. *C09K 3/18* (2013.01); *C07C 41/02* (2013.01); *C07C 41/03* (2013.01); *C07C 43/15* (2013.01); *C07C 303/34* (2013.01); *C07C 307/02* (2013.01); *C07F 9/00* (2013.01); *C08G 65/00* (2013.01); *C09D 133/066* (2013.01); *C09D 133/14* (2013.01); *C09K 3/16* (2013.01)

(58) Field of Classification Search
CPC ........... C09K 3/18; C07C 41/02; C07C 41/03; C07C 43/15
See application file for complete search history.

(56) References Cited

U.S. PATENT DOCUMENTS 5,990,342 A * 11/1999 Tsuzuki .................... C08F 2/26
560/183

FOREIGN PATENT DOCUMENTS

| CN | 104844747 A | | 8/2015 |
|---|---|---|---|
| JP | H08-034897 A | * | 8/1996 |
| JP | 2005-099381 A | * | 4/2005 |
| JP | 2015040264 A | | 3/2015 |
| TW | 201313677 | | 4/2013 |

OTHER PUBLICATIONS

Machine translation of JPH0834897, 1996, performed on Espacenet on Jul. 19, 2018.*
Machine translation of JP2005099381, 2005, performed on Espacenet on Jul. 19, 2018.*

* cited by examiner

*Primary Examiner* — Nicholas E Hill
(74) *Attorney, Agent, or Firm* — CKC & Partners Co., LLC

(57) ABSTRACT

The present invention relates to a method of producing an alkoxylene derivative and an application thereof. A mixture is firstly subjected to a first reaction for obtaining a first intermediate. The mixture includes an alkyl alcohol compound and a glycidyl ether compound. A second reaction is performed to the first intermediate and an epoxyalkyl compound, thereby obtaining the alkoxylene derivative. The alkoxylene derivative can effectively improve antistatic property and anti-fogging property.

5 Claims, 2 Drawing Sheets

100a performing a first reaction to a mixture, thereby forming a first intermediate — 110

performing a second reaction to the first intermediate and a an epoxyalkyl compound — 120

performing a third reaction to a product of the second reaction and an acidic compound, thereby forming a second intermediate — 121

performing a neutralization reaction to the second intermediate — 123

obtaining an alkoxylene derivative — 130

FIG. 2

METHOD OF PRODUCING ALKOXYLENE DERIVATIVE AND APPLICATION THEREOF

RELATED APPLICATIONS

This application claims priority to Taiwan Application Serial Number 104134917, filed on Oct. 23, 2015, which is herein incorporated by reference.

BACKGROUND

Field of Invention

The present invention relates to a method of producing alkoxylene derivative and application thereof. More particularly, the present invention provides a method of producing alkoxylene derivative and an application thereof for improving antistatic property and anti-fogging property.

Description of Related Art

With the attention to quality of life, opto-electric elements in the conventional electrical products are much smaller as the lighter and thinner electrical products are developed. However, the requirements of the applied environment are much severer depending on the less volume of the opto-electric elements.

When the opto-electric elements are applied in the environment with high temperature and high humidity, the fog easily condenses onto a surface of the element, thereby affecting the performance and further destroying the element. More particularly, in the field of displays, the fog affects the displaying of the display device, thereby decreasing the performance.

Moreover, the performances of the opto-electric elements are mainly achieved by the charge conduction, such that a steady electric environment contributes to enhance the properties of the opto-electric elements. However, the static electricity produced in the daily life often affects the opto-electric elements. Although the static electricity instantly discharges, the static electricity is high voltage. Therefore, the static electricity usually causes huge harm to the smaller opto-electric element.

In order to eliminate the damage of the fog or the static electricity for the opto-electric elements, an anti-fogging material or antistatic material can be disposed on a surface of the opto-electric element to prevent from the fog condensation or to eliminate the static electricity, thereby preventing the opto-electric element from damage.

The aforementioned anti-fogging material or antistatic material generally can be a composite film including an anti-fogging agent or an antistatic agent.

However, the conventional anti-fogging agent or the antistatic agent is uniformly mixed with the resin materials of the protective film by a physical method. Therefore, the anti-fogging agent or the antistatic agent migrates to the surface of the composite film with the variation of the temperature and humidity of the environment or the increase of the applied time, thereby decreasing the anti-fogging property and the antistatic property.

Besides, the anti-fogging agent or antistatic agent migrated to the surface also induces the defect of after-tack, thereby decreasing the surface property.

In view of this, there is an urgent need to provide a method of producing alkoxylene derivative and an application thereof for improving the disadvantages of the conventional method of producing alkoxylene derivative and the application thereof.

SUMMARY

Therefore, an aspect of the present invention is to provide a method of producing an alkoxylene derivative. The method can synthesize the alkoxylene derivative with excellent antistatic property and anti-fogging property by choosing monomers.

Another aspect of the present invention is to provide the alkoxylene derivative. The alkoxylene derivative is obtained by the aforementioned method.

Another aspect of the present invention is to provide a photo-curing resin composition. The photo-curing resin composition includes the alkoxylene derivative obtained by the aforementioned method.

Another aspect of the present invention is to provide a composite film. The composite film includes a photo-curing film formed by the aforementioned photo-curing resin composition.

According to the aforementioned aspect of the present invention, the method of producing the alkoxylene derivative is provided. A first reaction is firstly performed to a mixture, thereby forming a first intermediate. The mixture includes an alkyl alcohol compound shown as following formula (I) and a glycidyl ether compound shown as following formula (II):

$$R_1O\!-\!\!\left(\!R_2\!\right)_{\!x}\!\!-\!H \qquad (I)$$

in the formula (I), $R_1$ represents an alkyl group of 8 to 30 carbons; $R_2$ represents an alkoxylene group of 2 to 4 carbons, and an oxygen atom of the terminal group in $R_2$ is bonded with the hydrogen atom; and x represents an integer of 0 to 100.

$$\underset{H_2C-CH-R_3-R_4}{\overset{O}{\triangle}} \qquad (II)$$

in the formula (II), $R_3$ represents $$-\!\!-\!\mathrm{CH_2\!-\!O\!\!-\!\!\left(\!\overset{O}{\underset{\|}{C}}\!\right)_{\!r}\!\!-},$$

$C\!=\!O$ is bonded with $R_4$, and r represents 0 or 1. Furthermore, $R_4$ represents a functional group containing a $C\!=\!C$ unsaturated group.

Then, a second reaction is performed to the first intermediate and an epoxyalkyl compound, thereby forming the alkoxylene derivative. The epoxyalkyl compound includes an epoxyalkyl compound of 2 to 4 carbons.

According to an embodiment of the present invention, after the second reaction is performed, the method further comprises performing a third reaction to a product of the second reaction and an acidic compound, thereby forming a second intermediate. The second intermediate is subjected to a neutralization reaction, thereby obtaining the alkoxylene derivative.

According to another embodiment of the present invention, the aforementioned acidic compound includes a sulfonic acid compound, a phosphoric acid compound or a carboxylic compound.

According to yet another embodiment of the present invention, a neutralization agent of the aforementioned neutralization reaction is an alkali metal compound, an alkaline earth compound, an amine compound, an alkylamine compound, or an alkanolamine compound with or without an alkyl substituent.

According to the further aspect of the present invention, the alkoxylene derivative is provided. The alkoxylene derivative is obtained by the aforementioned method, and the structure of the alkoxylene derivative is shown as the following formula (III):

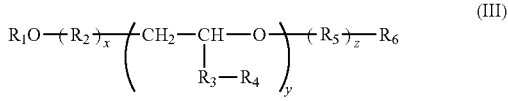  (III)

in the formula (III), $R_1$ represents an alkyl group of 8 to 30 carbons; $R_2$ represents an alkoxylene group of 2 to 4 carbons, and the alkylene group in $R_2$ is bonded with $R_1O$—; $R_3$ represents

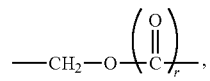

$C=O$ is bonded with $R_4$, and r represents 0 or 1; $R_4$ represents a functional group containing a $C=C$ unsaturated group; $R_5$ represents an alkoxylene group of 2 to 4 carbons, and an oxygen atom of the terminal group in $R_5$ is bonded with $R_6$; $R_6$ represents a hydrogen atom; x represents an integer of 0 to 100; y represents an integer of 1 to 10; and z represents an integer of 1 to 100.

According to the further aspect of the present invention, the alkoxylene derivative is provided. The alkoxylene derivative is obtained by the aforementioned method, and the structure of the alkoxylene derivative is shown as the following formula (IV):

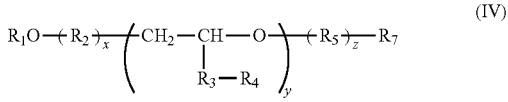  (IV)

in the formula (IV), $R_1$ represents an alkyl group of 8 to 30 carbons; $R_2$ represents an alkoxylene group of 2 to 4 carbons, and the alkylene group in $R_2$ is bonded with $R_1O$—; $R_3$ represents

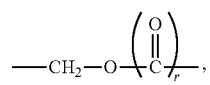

$C=O$ is bonded with $R_4$, and r represents 0 or 1; $R_4$ represents a functional group containing a $C=C$ unsaturated group; $R_5$ represents an alkoxylene group of 2 to 4 carbons, and an oxygen atom of the terminal group in $R_5$ is bonded with $R_7$; $R_7$ represents an anionic group; x represents an integer of 0 to 100; y represents an integer of 1 to 10; and z represents an integer of 1 to 100.

According to an embodiment of the present invention, the aforementioned anionic group can include but be not limited to —$SO_3M$, —$PO_3M_2$, —$PO_3MH$, —COOM or an other suitable anionic groups. M represents a hydrogen atom, an alkali metal atom, (an alkaline earth atom)$_{1/2}$, an ammonium group, an alkyl ammonium, or an alkanolammonium compound with or without an alkyl substituent.

According to the further aspect of the present invention, the photo-curing resin composition is provided. The photo-curing resin composition includes a photo-curing resin and the alkoxylene derivative obtained by the aforementioned method. Based on an amount of the phot-curing resin as 100 parts by weight, an amount of the alkoxylene derivative is 0.2 to 15 parts by weight.

According to the further aspect of the present invention, the composite film is provided. The composite film includes a substrate and the photo-curing film disposed on a surface of the substrate. The photo-curing film is formed by subjecting the photo-curing resin composition to a photo-curing process, and a contact angle of the photo-curing film relative to water is not larger than 30 degrees.

According to an embodiment of the present invention, a first surface electric resistance of the composite film is less than $10^{11}$ ohm/□ (i.e. the first surface electric resistance of per unit area of the composite film is less than $10^{11}$ ohm).

According to another embodiment of the present invention, while the composite film is placed in an environment at 65° C. and 95% relative humidity, a second surface electric resistance of the composite film is less than $10^{11}$ ohm/□, and a ratio of the second surface electric resistance to the first surface electric resistance is less than 100 and larger than 0.

According to yet another embodiment of the present invention, the ratio of the second surface electric resistance to the first surface electric resistance is less than 20 and larger than 0.

According to yet another embodiment of the present invention, the ratio of the second surface electric resistance to the first surface electric resistance is less than or equal to 16 and larger than 0.

In the method of the alkoxylene derivative and the application thereof of the present invention, the alkoxylene derivative is synthesized by specific reactants, and the alkoxylene derivative can form a covalent bond with a unsaturated group of a resin material, thereby having excellent aging stability.

BRIEF DESCRIPTION OF THE DRAWINGS

The invention can be more fully understood by reading the following detailed description of the embodiment, with reference made to the accompanying drawings as follows:

FIG. 2 is a flow chart of the method of producing the alkoxylene derivative according to another embodiment of the present invention.

DETAILED DESCRIPTION

Figure 1:
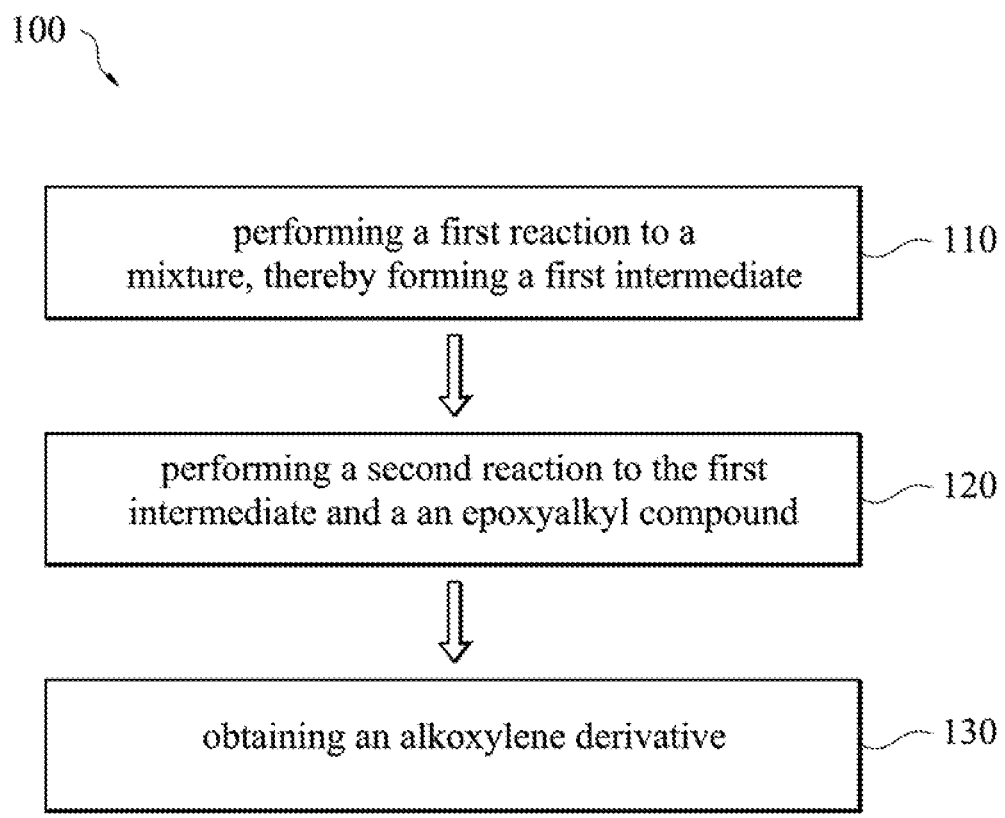
FIG. 1 is a flow chart of the method of producing the alkoxylene derivative according to one of the embodiments of the present invention.

In the following description, several specific details are presented to provide a thorough understanding of the fabrication and applications according to the embodiments of the present invention. One skilled in the relevant art will recognize, however, that the embodiments of the present invention provide many applicable inventive concepts that can be practiced in various specific contents. The specific embodiments discussed hereinafter are used for explaining but not limited to the scope of the present invention.

The term "after-tack" of the present invention is a surface defect of adhering due to temperature and humidity, or induced by an anti-fogging agent or an antistatic agent migrated to a surface of the composite film, such that a surface of a coating film easily adhered to pollution, or a flattening property of the surface is decreased, thereby decreasing a surface property of the coating film.

The structure of the alkoxylene derivative of the present invention is shown as the following formula (VII):

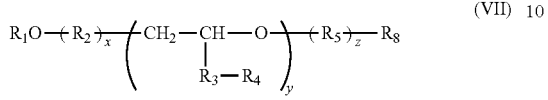

(VII)

in the formula (VII), $R_1$ represents an alkyl group of 8 to 30 carbons; $R_2$ represents an alkoxylene group of 2 to 4 carbons, and the alkylene group in $R_2$ is bonded with $R_1O—$; $R_3$ represents

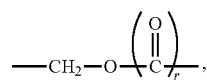

wherein C=O is bonded with $R_4$, and r represents 0 or 1; $R_4$ represents a functional group containing a C=C unsaturated group; $R_5$ represents an alkoxylene group of 2 to 4 carbons, and an oxygen atom of the terminal group in $R_5$ is bonded with $R_8$; $R_8$ represents a hydrogen atom or an anionic group; x represents an integer of 0 to 100; y represents an integer of 1 to 10; and z represents an integer of 1 to 100.

Please refer to FIG. 1, which is a flow chart of the method of producing the alkoxylene derivative according to an embodiment of the present invention. In an embodiment, the method 100 is firstly performed a first reaction to a mixture, thereby forming a first intermediate as shown in a process 110.

The aforementioned mixture includes an alkyl alcohol compound shown as following formula (I) and a glycidyl ether compound shown as following formula (II):

(I)

in the formula (I), $R_1$ represents an alkyl group of 8 to 30 carbons; $R_2$ represents an alkoxylene group of 2 to 4 carbons, and an oxygen atom of the terminal group in $R_2$ is bonded with the hydrogen atom; and x represents an integer of 0 to 100.

When $R_1$ represents the alkyl group of 8 to 30 carbons, the aforementioned alkyl group of 8 to 30 carbons can include a linear alkyl group or a branch alkyl group. The alkyl group of 8 to 30 carbons can include but be not limited to n-octyl, iso-octyl, 2-ethyl hexyl, n-nonyl, iso-nonyl, 2-methyl octyl, 3-methyl octyl, 4-methyl octyl, 5-methyl octyl, 6-methyl octyl, 2-ethyl heptyl, 3-ethyl heptyl, 4-ethyl heptyl, 5-ethyl heptyl, 2-propyl hexyl, 3-propyl hexyl, n-decyl, iso-decyl, 2-methyl nonyl, 3-methyl nonyl, 4-methyl nonyl, 5-methyl nonyl, 6-methyl nonyl, 7-methyl nonyl, 2-ethyl octyl, 3-ethyl octyl, 4-ethyl octyl, 5-ethyl octyl, 6-ethyl octyl, 2-propyl heptyl, 3-propyl heptyl, 4-propyl heptyl, 2-butyl hexyl, n-hendecyl, n-dodecyl, n-tridecyl, n-tetradecyl, 2-pentyl nonyl, n-pentadecyl, n-hexadecyl, n-heptadecyl, n-octadecyl, n-nonadecyl, n-eicosyl, n-heneicosyl, n-docosyl, n-tricosyl, n-tetracosyl, n-pentacosyl or the like.

In an embodiment, $R_1$ preferably represents an alkyl group of 8 to 25 carbons, and more preferably represents an alkyl group of 8 to 18 carbons.

When the carbon number of $R_1$ is less than 8, the alkoxylene derivative has a defect of poor surface activity, thereby decreasing an emulsifying property, a dispersing property, a resin-compatibility and a polymerization stability of the alkoxylene derivative, further hardly mixing uniformly with a photo-curing resin, thus hardly forming a photo-curing film.

When $R_2$ represents the alkoxylene group of 2 to 4 carbons, the aforementioned alkoxylene of 2 to 4 carbons can include but be not limited to ethoxylene, propoxylene, iso-propoxylene, butoxylene, iso-butoxylene, sec-butoxylene, tert-butoxylene or a combination thereof.

In an embodiment, x preferably can be an integer of 0 to 50, and more preferably can be an integer of 0 to 30.

$R_2$ segment can enhance hydrophilic property of the alkoxylene derivative, thereby improving an anti-fogging property and antistatic property.

If x is larger than 100, a longer $R_2$ segment can decrease the resin-compatibility of the alkoxylene derivative, thereby subjecting a surface of the photo-curing film to be hardly dried, further inducing the defect of after-tack, thus decreasing the anti-fogging property and antistatic property.

The aforementioned alkyl alcohol compound shown as formula (I) can include but be not limited to n-decanol, lauryl alcohol, n-tetradecanol, n-hexadecanol, fatty alcohol polyoxyethylene ether, fatty alcohol polyoxypropylene ether, an other suitable alkyl alcohol compound or a combination thereof.

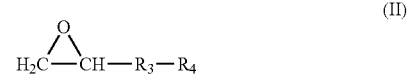

(II)

in the formula (II), $R_3$ represents

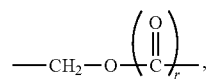

C=O is bonded with $R_4$, and r represents 0 or 1; and $R_4$ represents a functional group containing a C=C unsaturated group.

When r is 0, the alkoxylene derivative has a structure of alkene group; and when r is 1, the alkoxylene derivative has a structure of acrylic group. When r is 0 or 1, the alkene or the acrylic group with a double bond structure can be subjected to a polymerization reaction with an unsaturated monomer, thereby subjecting the alkoxylene derivative and the photo-curing resin to form a bonding, further enhancing the aging stability.

The aforementioned functional group containing a C=C unsaturated group can include an alkylene group of 2 to 4 carbons with at least one substituent or without substituents. The alkylene group of 2 to 4 carbons with at least one substituent or without substituents can include but be not limited to ethylene, propylene, iso-butylene, acrylate group, methacrylate group or an other suitable groups.

Preferably, the aforementioned functional group containing a C=C unsaturated group can include an alkylene group of 2 to 4 carbons. More preferably, the aforementioned functional group containing a C=C unsaturated group can include an alkylene group of 3 carbons.

The glycidyl ether compound shown as formula (II) can include but be not limited to allyl glycidyl ether, glycidyl methacrylate, isobutylene glycidyl ether, an other suitable glycidyl ether compound or a combination thereof.

Based on an amount of the alkyl alcohol compound shown as formula (I) as 100 parts by weight, an amount of the glycidyl ether compound shown as formula (II) is 29 to 116 parts by weight, preferably is 41 to 87 parts by weight, and more preferably is 47 to 70 parts by weight.

In an embodiment, the alkyl alcohol compound shown as formula (I) reacts with the glycidyl ether compound shown as formula (II), further forming a covalent bond between the opened ring structure and the alkyl alcohol compound, thus obtaining the first intermediate.

When the first reaction is performed, in order to accelerate the reaction rate, the aforementioned mixture can include catalyst to decrease the reaction temperature and the reaction time. Besides enhancing the yield, the catalyst can also decrease the color (the hue) of the first intermediate, thereby preventing the coated material from being affected by the alkoxylene derivative. The catalyst can include triphenylphosphine, triethylamine, sodium hydroxide, potassium hydroxide, aluminum chloride, boron trifluoride, tetraalkylammonium salt, tin tetraisopropoxide, zinc perchlorate or the like. Preferably, the catalyst can include triphenylphosphine, potassium hydroxide, boron trifluoride, tetraalkylammonium salt or the like. More preferably, the catalyst can be boron trifluoride.

Based on the amount of the alkyl alcohol compound shown as formula (I) as 100 parts by weight, an amount of the catalyst is 0.01 to 5 parts by weight, preferably is 0.02 to 3 parts by weight, and more preferably is 0.05 to 2 parts by weight.

When the aforementioned mixture includes the catalyst, the reaction temperature of the first reaction can be 60° C. to 100° C., and the reaction time can be 4 hours to 8 hours. Preferably, the reaction temperature of the first reaction can be 70° C. to 90° C., and the reaction time can be 4 hours to 6 hours. More preferably, the reaction temperature of the first reaction can be 85° C., and the reaction time can be 5 hours.

The structure of the aforementioned first intermediate is shown as the following formula (V):

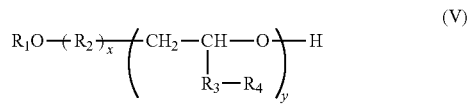

(V)

in the formula (V), the definitions of $R_1$, $R_2$, $R_3$, $R_4$ and x are the same as above rather than focusing or mentioning them in details; and y represents an integer of 1 to 10.

In an embodiment, y preferably can be an integer of 1 to 10, and more preferably can be an integer of 1 to 3.

If y is larger than 10, based on the same weight, the alkoxylene derivative has less ratio of hydrophilic groups, thereby decreasing the anti-fogging property and antistatic property of the photo-curing film; and a crosslinking degree of the alkoxylene derivative and the monomer will increase, thereby increasing a shrinkage percentage of the coated film, thus affecting the coating property of the photo-curing film.

After the process 110 is performed, a second reaction is performed to the aforementioned first intermediate and an epoxyalkyl compound, thereby obtaining the alkoxylene derivative shown as following formula (III), as shown in processes 120 and 130. The epoxyalkyl compound includes an epoxyalkyl compound of 2 to 4 carbons:

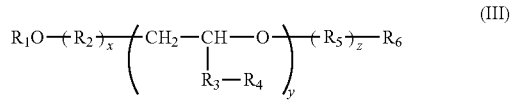

(III)

in the formula (III), definitions of $R_1$, $R_2$, $R_3$, $R_4$, x and y are the same as above; $R_5$ represents an alkoxylene group of 2 to 4 carbons, and an oxygen atom of the terminal group in $R_5$ is bonded with $R_6$; $R_6$ represents a hydrogen atom; and z represents an integer of 1 to 100.

z preferably represents an integer of 1 to 30 carbons, and more preferably represents an integer of 1 to 10.

If z is larger than 100, an excessively long $R_5$ segment subjects the alkoxylene derivative to have poor resin-compatibility, thereby subjecting the surface of the photo-curing film to be hardly dried, further inducing the defect of after-tack, and the photo-curing film has poor anti-fogging property and antistatic property. If z is smaller than 1, the alkoxylene derivative has less hydrophilic group, thereby decreasing the anti-fogging property and antistatic property of the photo-curing film.

A sum of x and z generally is an integer of 1 to 100, preferably is an integer of 1 to 50, and more preferably is an integer of 10 to 40.

When the sum of x and z is an integer of 10 to 40, the alkoxylene derivative can have much better antistatic property.

In an embodiment, the aforementioned second reaction is a polymerization reaction performed with epoxyalkyl compound and the first intermediate by ring-opening reaction, thus obtaining the alkoxylene derivative shown as formula (III).

Please refer to FIG. 2, which is a flow chart of the method of producing the alkoxylene derivative according to another embodiment of the present invention. A method 100a is substantially similar to the method 100 in procedure, but the difference between method 100 and 100a is that the method 100a further comprises process 121 and process 123 after the process 120 is performed.

In an embodiment, when the process 121 is performed, a product of the second reaction further subjects to a third reaction with an acidic compound, thereby forming a second intermediate.

The aforementioned acidic compound can include a sulfonic acid compound, a phosphoric acid compound, a carboxylic compound or an other acidic compound.

When the aforementioned acidic compound is the sulfonic acid or the phosphoric acid compound, the alkoxylene derivative can have much better antistatic property.

When the third reaction is performed, the acidic compound subjects to an esterification reaction with a hydroxyl-terminated group of the aforementioned product of the second reaction, thereby synthesizing the second intermediate.

After the process 121 is performed, a neutralization reaction is performed to the second intermediate, thereby obtaining the alkoxylene derivative shown as following formula (IV), as shown in a processes 130 and 130:

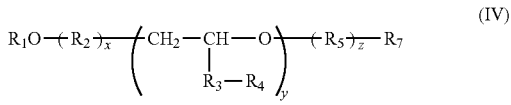

$$(IV)$$

in the formula (IV), the definitions of $R_1$, $R_2$, $R_3$, $R_4$, $R_5$, x, y and z are the same as the above; and $R_7$ represents an anionic group.

In formula (IV), a sum of x and z generally is an integer of 1 to 100, preferably is an integer of 1 to 30, and more preferably is an integer of 2 to 10. When the sum of x and z is an integer of 2 to 10, the alkoxylene derivative can have much better antistatic property and anti-fogging property.

In an embodiment, a neutralization agent of the neutralization reaction can include an ammonia, an alkali metal compound, an alkaline earth compound, an amine compound, an alkylamine compound, an alkanolamine compound with or without an alkyl substituent, an other suitable alkali compound or a combination thereof.

Based on the various combination of the acidic compound and the neutralization agent of the third reaction, $R_7$ can represent —$SO_3M$, —$PO_3M_2$, —$PO_3MH$ or —COOM, and M can be a hydrogen atom, an alkali metal atom, (an alkaline earth atom)$_{1/2}$, an ammonium group, an alkyl ammonium, or a alkanolammonium compound with or without an alkyl substituent.

When the method of producing the alkoxylene derivative of the present invention further comprises the neutralization reaction, the alkoxylene derivative has better stability, such that the alkoxylene derivative can be applied in an environment with high temperature and high humidity, thereby efficiently enhancing the stability of an applied product. Moreover, the neutralized alkoxylene derivative has the anionic group, thereby efficiently enhancing charge conducting ability, further improving antistatic property.

In an embodiment, when the neutralization agent is ammonia water, although the neutralization reaction produces an escaping ammonia gas, the alkoxylene derivative has excellent anti-fogging property and antistatic property, and the anti-fogging property has well stability.

Preferably, when the aforementioned neutralization agent is the alkanolamine compound with or without an alkyl substituent, the neutralization reaction does not produce the escaping ammonia gas because the alkanolamine compound with or without an alkyl substituent has better stability, such that the neutralization agent (i.e. the hydrammonium compound with or without an alkyl substituent) can eliminate harm of the process to operators and environment, and the alkoxylene derivative has better aging stability.

When the aforementioned alkanolamine compound with or without an alkyl substituent is a secondary alkanolamine compound, the alkoxylene derivative has much better aging stability.

In one example, the photo-curing resin composition of the present invention can include a photo-curing resin and the aforementioned alkoxylene derivative. Based on an amount of the photo-curing resin as 100 parts by weight, the amount of the alkoxylene derivative is 0.2 to 15 parts by weight, preferably is 0.2 to 12 parts by weight, and more preferably is 0.5 to 10 parts by weight.

When the amount of the alkoxylene derivative is larger than 15 parts by weight, after the photo-curing resin composition is coated to form a film, the coated film easily has the defect of after-tack. When the amount of the alkoxylene derivative is less than 0.2 parts by weight, the less alkoxylene derivative cannot efficiently improve the efficacy of the photo-curing resin composition.

In an embodiment, when the aforementioned photo-curing resin composition is exposed to ultraviolet light or other radiation, the double bond structure of the photo-curing resin will be subjected to the polymerization reaction, and the alkoxylene derivative containing the double bond groups [i.e. the aforementioned double bond groups of $R_4$ in the formula (III) and formula (IV)] will also participate in the polymerization reaction, thereby forming a bonding between the alkoxylene derivative and the photo-curing resin, further enhancing the aging stability.

In another embodiment, the aforementioned photo-curing resin composition can be coated onto a surface of a substrate, and then be subjected to a photo-curing process to form a photo-curing film, thereby obtaining a composite film (i.e. a film includes the substrate and the photo-curing film). A first surface electric resistance of the composite film is less than $10^{11}$ ohm/□. Thus, the composite film has excellent antistatic property.

In an embodiment, the aforementioned substrate can include but be not limited to an optical film, a glass substrate, a plastic substrate, a wooden substrate, a solar energy opto-electronic substrate, an other suitable substrate or a combination thereof.

Moreover, because the alkoxylene derivative of the present invention has a non-ionic group [such as the alkoxylene derivative shown as formula (III)] or an anionic group [such as the alkoxylene derivative shown as formula (IV)], the photo-curing film has better anti-fogging property, thereby improving the anti-fogging property of the composite film. In an embodiment, a contact angle of the photo-curing film relative to water is smaller than or equal to 30 degrees, preferably is smaller than or equal to 20 degrees, and more preferably is smaller than or equal to 10 degrees. When the contact angle of the photo-curing film relative to water exceeds (i.e. is larger than) 30 degrees, the anti-fogging property of the photo-curing film is poor.

Based on the aforementioned description, when the photo-curing resin composition is subjected to the photo-curing process, the double bond group of the alkoxylene derivative will be subjected to the polymerization reaction with the double bond of the photo-curing resin, thereby forming a bonding. Therefore, the photo-curing resin containing the alkoxylene derivative has better aging stability.

Accordingly, while the composite film of the present invention is placed in an environment with high temperature and high humidity, the surface electric resistance of the composite film can be less than $10^{11}$ ohm/□, the variation of the surface electric resistance is less than 100 and larger than 0, and the composite film still has excellent anti-fogging property. Therefore, the alkoxylene derivative of the present invention has excellent aging stability.

Preferably, the aforementioned variation of the surface electric resistance is less than 20 and larger than 0. More preferably, the aforementioned variation of the surface electric resistance is less than 16 and larger than 0.

In another embodiment, after the composite film of the present invention is placed in the environment with high temperature and high humidity for a long term, the surface electric resistance of the composite film may be less than the surface electric resistance of the composite film prior to be placed in the environment. It is because the composite film will absorb the moisture in the environment while the composite film is placed in the environment with high temperature and high humidity for a long term. Therefore, an amount of the hydrophilic groups in the composite film increases, thereby decreasing the surface electric resistance.

In one applied example, in addition to applying in coating industry, the photo-curing resin composition of the present invention can be coated onto any suitable substrates for providing excellent antistatic property and anti-fogging property.

Several embodiments are described below to illustrate the application of the present invention. However, these embodiments are not used for limiting the present invention. For those skilled in the art of the present invention, various alterations and modifications can be made without departing from the spirit and scope of the present invention.

Production of Photo-Curing Resin

The photo-curing resin of Synthesis Examples R-1 and R-2 were fabricated according to Table 1 as follows. According to the compositions and amounts thereof cited in Table 1, the photo-curing resin of Synthesis Examples R-1 and R-2 were mixed uniformly by a mixer at room temperature, thereby obtaining the photo-curing resin of Synthesis Examples R-1 and R-2.

Producing Alkoxylene Derivative

Synthesis Example S-1-1

Firstly, the catalyst was added into 1 mole (158 g) of n-decanol to form a mixture, and 1 mole (114 g) of allyl glycidyl ether was dropped into the mixture. Then, the mixture was heated to 85° C. and subjected to a first reaction. After 5 hours, a first intermediate of Synthesis Example S-1-1 was obtained. Next, 10 moles (440 g) of ethylene oxide was added into the first intermediate of Synthesis Example S-1-1, and then heated to 120° C. to perform a second reaction. After 2 hours, the alkoxylene derivative of Synthesis Example S-1-1 shown as the following formula (III-1) was obtained:

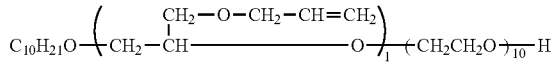

(III-1)

Synthesis Examples S-1-2 and S-1-3

Synthesis Examples S-1-2 and S-1-3 were practiced with the same method as in Synthesis Example S-1-1 by using various kinds or amounts of the components for the alkoxylene derivative and the reaction parameters. The alkoxylene derivatives of Synthesis Examples S-1-2 and S-1-3 respectively are shown as the following formula (III-2) and formula (III-3):

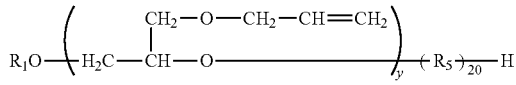

(III-2)

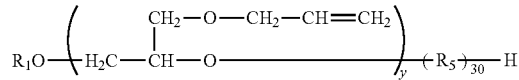

(III-3)

in the formula (III-2) and formula (III-3), definitions of $R_1$, $R_5$ and y were the same as the above rather than focusing or mentioning them in details.

Synthesis Example S-2-1

Firstly, the catalyst was added into 1 mole (242 g) of n-hexadecanol to form a mixture, and 1.5 moles (171 g) of allyl glycidyl ether was dropped into the mixture. Then, the mixture was heated to 85° C. and subjected to a first reaction. After 5 hours, a first intermediate of Synthesis Example S-2-1 was obtained. Next, 5 moles (220 g) of ethylene oxide was added into the first intermediate of Synthesis Example S-2-1, and then heated to 120° C. for performing a second reaction. After 2 hours, a second reaction product of Synthesis Example S-2-1 was obtained.

1 mole (97 g) of sulfamic acid was added into the aforementioned second reaction product of Synthesis Example S-2-1 and heated to 90° C. to perform the third reaction. After 5 hours, an ammonia water was added to perform a neutralization reaction, thereby obtaining the alkoxylene derivative shown as the following formula (IV-1) of Synthesis Example S-2-1:

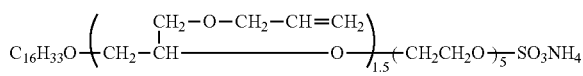

(IV-1)

Synthesis Example S-2-2

Firstly, the catalyst was added into 1 mole (186 g) of n-dodecanol to form a mixture, and 1.3 moles (148 g) of allyl glycidyl ether was dropped into the mixture. Then, the mixture was heated to 85° C. and subjected to a first reaction. After 5 hours, a first intermediate of Synthesis Example S-2-2 was obtained. Next, 10 moles (440 g) of ethylene oxide was added into the first intermediate of Synthesis Example S-2-2, and then heated to 120° C. to perform the second reaction. After 2 hours, a second reaction product of Synthesis Example S-2-2 was obtained.

1 mole (97 g) of sulfamic acid was added into the aforementioned second reaction product of Synthesis Example S-2-2 and heated to 90° C. to perform the third reaction. After 5 hours, a monoethanolamine was added to perform a neutralization reaction, thereby obtaining the alkoxylene derivative shown as the following formula (IV-2) of Synthesis Example S-2-2:

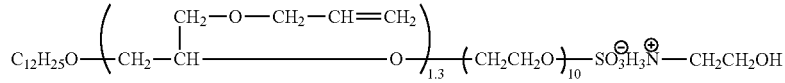

(IV-2)

Synthesis Examples S-2-3 to S-2-6

Synthesis Examples S-2-3 to S-2-6 were practiced with the same method as in Synthesis Example S-2-1 by using various kinds or amounts of the components for the alkoxylene derivative. The second intermediate of Synthesis Example S-2-3 was neutralized by the ammonia water. The second intermediate of Synthesis Examples S-2-4 and S-2-5 were neutralized by the alkanolamine compound with or without an alkyl substituent, and the third reaction in Synthesis Example S-2-5 was performed by polyphosphoric acid compound or phosphorus pentoxide. The second intermediate of Synthesis Example S-2-6 was neutralized by the ammonia water. The alkoxylene derivatives of Synthesis Examples S-2-3 to S-2-6 are respectively shown as the following formula (IV-3) to formula (IV-6). Due to the affection of the reaction parameters, the structure of the alkoxylene derivative of Synthesis Example S-2-5 is shown as the following formula (IV-5-1) and (IV-5-2):

added into a mixer at room temperature and uniformly mixed, thereby obtaining the photo-curing resin composition of Example 1-1.

Then, the aforementioned photo-curing resin composition was coated onto a substrate. The coated substrate was exposed to ultraviolet light to form a photo-curing film, thereby obtaining the composite film of Example 1. The resulted composite film was evaluated according to the following evaluation method, and the result thereof was listed as Table 2. The evaluation methods of the surface property, the adhering property, the antistatic property, the anti-fogging property and the aging test were described as follows.

Examples 1-2 to 1-6 and 2-1 to 2-12 and Comparative Examples 1 to 6

Examples 1-2 to 1-6 and 2-1 to 2-12 and Comparative Examples 1 to 6 were practiced with the same method as in

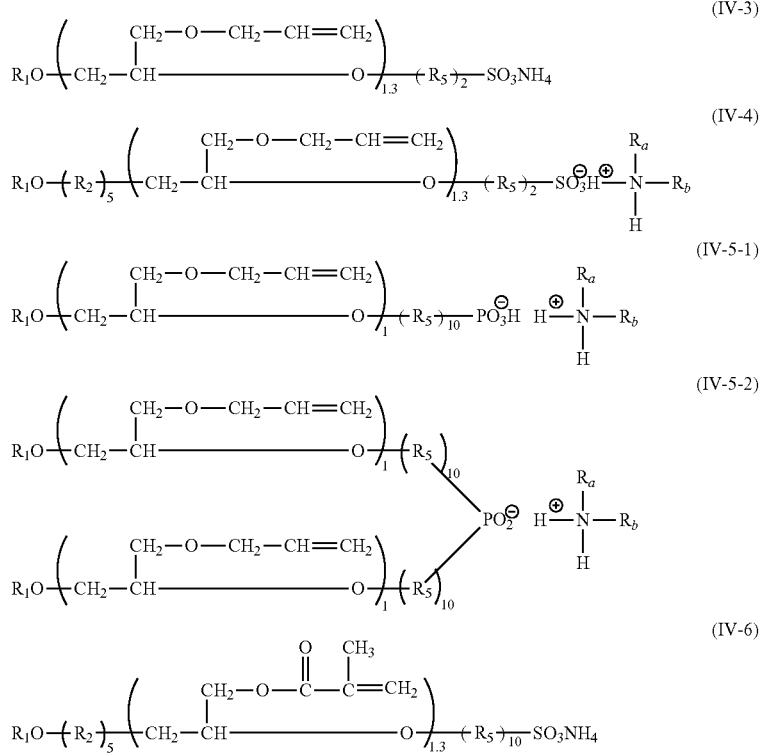

in formula (IV-3) to formula (IV-6), definitions of $R_1$, $R_2$, $R_5$ and y were the same as the above rather than focusing or mentioning them in details. $R_a$ and $R_b$ respectively represented methyl, ethyl, propyl, methylol, ethylol, propylol, iso-propylol or the like.

Production of Composite Film

The composite films of Examples 1-1 to 1-6 and 2-1 to 2-12 and Comparative Examples 1 to 6 were manufactured according to Tables 2 to 4 as follows.

Example 1-1

100 parts by weight of the photo-curing resin (R-1) and 0.5 parts by weight of the alkoxylene derivative (S-1-1) were Example 1-1 by using various kinds of the alkoxylene derivative. The formulations and evaluating results thereof were listed in Tables 2 to 4 rather than focusing or mentioning them in details.

Evaluation Methods

1. Surface Property

The photo-curing resin composition of the aforementioned Examples 1-1 to 1-6 and 2-1 to 2-12 and Comparative Examples 1 to 6 were uniformly coated onto a polyethylene terephthalate (PET) film by the #4 coating rod. After the coated film was cured by ultraviolet light, the photo-curing film with a thickness of 10 μm was obtained. And then, the photo-curing film was directly touched by hand to evaluate the film is dried or not, and an evaluation was made according to the following criterion:

○: the surface was completely dried;

Δ: the surface was not completely dried;

x: the surface was after-tack.

2. Adhering Property

According to the adhesiveness testing method, JIS.5400 (1900)8.5, the photo-curing films of the aforementioned Examples 1-1 to 1-6 and 2-1 to 2-12 and Comparative Examples 1 to 6 were cut into 100 grid patterns by a knife. Next, the grid patterns were adhered by a tape, and then the tape was removed. An evaluation was made according to the residual grid patterns and the following criterion:

○: 5B;

Δ: 4B;

x: 3B to 0B.

Wherein, 5B: the grid patterns do not fall;

4B: 0%<the amount of the fallen grid patterns≤5%;

3B: 5%<the amount of the fallen grid patterns≤15%;

2B: 15%<the amount of the fallen grid patterns≤35%;

1B: 35%<the amount of the fallen grid patterns≤65%;

0B: 65%<the amount of the fallen grid patterns≤100%.

3. Antistatic Property

A surface electric resistance of the composite film of the aforementioned Examples 1-1 to 1-6 and 2-1 to 2-12 and Comparative Examples 1 to 6 were measured by a surface resistance testing meter (manufactured by Static Solution Inc. and the trade name is RT-1000), and an evaluation was made according to the following criterion. The voltage of the resistance testing meter was set to 110 voltage:

⊚: the surface electric resistance<$10^{10}$;

○: $10^{10}$≤the surface electric resistance<$10^{11}$;

Δ: $10^{11}$≤the surface electric resistance<$10^{12}$;

x: $10^{12}$≤the surface electric resistance.

4. Anti-Fogging Property

Before performing the anti-fogging test, the beaker was filled with water heated to 80° C. The composite film of the aforementioned Examples 1-1 to 1-6 and 2-1 to 2-12 and Comparative Examples 1 to 6 were placed over the beaker (with coated side facing the water surface) and the surface of the samples were about 5 cm away from the water level. Once the composite film was placed over the beaker, it was pressed firmly near the edges to make there was no air gap between the sample and the beaker. Then the composite film was held at the beaker for 30 seconds to observe if the sample fogs or not. The evaluation of anti-fogging was made according to the following criterion:

○: Clear water film was formed, and there was no fog observed on the surface;

Δ: Spotted film was formed by large or small drops of water;

x: Fog was observed on the surface.

5. Contact Angle

The contact angle of the photo-curing film relative to water was measured by conventional method and instrument rather than focusing or mentioning them in details.

6. Aging Test

The composite film of the aforementioned Examples 2-1 to 2-12 and Comparative Examples 1 to 6 was placed in an environment at 65° C. with humidity of 95%. After 500 hours, the composite was sequentially subjected to the aforementioned evaluation methods. The evaluation method of the variation of surface electric resistance was calculated according to the following formula (VI), and an evaluation was made according to the following criterion:

$$\text{variation of surface electric resistance} = \frac{\text{electric resistance after aging test}}{\text{electric resistance before aging text}} \quad \text{(VI)}$$

○: 0<the variation of the surface electric resistance<100;

Δ: 100≤the variation of the surface electric resistance.

Please refer to Table 2, because the alkoxylene derivatives of Examples 1-1 to 1-6 lacked ionic group, the composite film had poor charge conducting ability, thereby subjecting the charge to easily be accumulated, thus easily inducing the static electricity. However, based on the evaluating result of the contact angle, in Examples 1-1 to 1-6, the contact angle of the photo-curing film relative to water was not larger than 20 degrees, such that the alkoxylene derivative can efficiently eliminate the fog, thereby improving the anti-fogging property of the composite film.

Based on the evaluating result of the surface property of Examples 1-1 to 1-3, because the alkoxylene derivative and the photo-curing resin had poor compatibility, such that a surface of the composite film was not completely dried, thereby decreasing the performance of the surface property.

Moreover, please refer to Table 3, the alkoxylene derivatives of the Examples 2-1 to 2-12 had anionic group, thereby increasing the charge conducting ability, further decreasing the surface electric resistance, such that the composite film of Examples 2-1 to 2-12 had better antistatic property.

In Example 2-2, because the photo-curing resin had poor compatibility with the alkoxylene derivatives, the surface electric resistance of the composite film of Example 2-2 was higher, thereby decreasing the antistatic property. However, after the aging test, the alkoxylene derivative of Example 2-2 had steady static variation. Therefore, the alkoxylene derivative of Example 2-2 had better aging stability.

Furthermore, when the neutralization agent of the neutralization reaction in the method of producing the alkoxylene derivative was the alkanolamine compound with or without an alkyl substituent, the obtained alkoxylene derivative had much better aging stability. Therefore, the alkoxylene derivative had excellent antistatic property and aging stability.

Besides, based on the evaluating result of the anti-fogging property and the contact angle, the composite film of Examples 2-1 to 2-12 can efficiently prevent the fog from being condensed onto the surface, thereby having better anti-fogging property. After the aging test, the composite film still had excellent anti-fogging property.

Please refer to Table 4, in Comparative Examples 1 and 4, when the photo-curing resin composition did not include the alkoxylene derivative of the present invention, the composite film cannot efficiently eliminate the fog to be condensed onto the surface, and the charge conducting ability of the composite film was poorer. Therefore, the composite film of Comparative Examples 1 and 4 had defects of poor anti-fogging property and antistatic property.

Although the alkoxylene derivative of Comparative Examples 2 and 5 can improve the effect of the composite film before the aging test, the photo-curing film was after-tack after the aging test. It is because the alkoxylene derivative of Comparative Examples 2 and 5 was physically mixed with the photo-curing resin, such that the alkoxylene derivative did not chemically bond to the photo-curing resin, thereby hardly eliminating the defects induced by the migration of the alkoxylene derivative.

According to Examples and Comparative Examples of the present invention, the alkoxylene derivative of the present invention can efficiently enhance the antistatic property and anti-fogging property of the composite film. Further, the double bond group of the alkoxylene derivative can further form a bonding with the photo-curing resin. Therefore, the alkoxylene derivative can overcome the defect of the migration of the conventional alkoxylene derivative, thereby improving the aging stability.

Moreover, when the method of producing the alkoxylene derivative further includes the neutralization reaction, the alkoxylene derivative can have better aging stability. If the neutralization agent of the neutralization reaction is the alkanolamine compound of the present invention, the alkoxylene derivative has much better aging stability.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims.

TABLE 1

| Composition (parts by weight) | Synthesis Example R-1 | Synthesis Example R-2 |
|---|---|---|
| CN104 | 47 | 22.5 |
| SR339 | 40 | 27 |
| SR349 | 10 | 18 |
| EM2105 |  | 27 |
| Irgacure 184 | 2.5 | 4.5 |
| Darocu TPO | 0.5 | 1 |

CN104 Photo-curing resin manufactured by Sartomer Co., LTD.
SR339 Photo-curing resin manufactured by Sartomer Co., LTD.
SR349 Photo-curing resin manufactured by Sartomer Co., LTD.
EM2105 o-phenylphenol EO acrylate (manufactured by Eternal Materials Co., Ltd.)
Irgacure 184 Photo-curing resin manufactured by BASF Co., LTD.
Darocur TPO Photo-curing resin manufactured by BASF Co., LTD.

TABLE 2

| | | | Example 1-1 | Example 1-2 | Example 1-3 | Example 1-4 | Example 1-5 | Example 1-6 |
|---|---|---|---|---|---|---|---|---|
| Composition (parts by weight) | Photo-curing Resin | R-1 | 100 | 100 | 100 | | | |
| | | R-2 | | | | 100 | 100 | 100 |
| | Surfactant | S-1-1 | 0.5 | | | 0.5 | | |
| | | S-1-2 | | 0.5 | | | 0.5 | |
| | | S-1-3 | | | 0.5 | | | 0.5 |
| | | S-2-1 | | | | | | |
| | | S-2-2 | | | | | | |
| | | S-2-3 | | | | | | |
| | | S-2-4 | | | | | | |
| | | S-2-5 | | | | | | |
| | | S-2-6 | | | | | | |
| | | S-3-1 | | | | | | |
| | | S-3-2 | | | | | | |
| Evaluation Method | Before Aging Test | Surface Property | Δ | Δ | Δ | ○ | ○ | ○ |
| | | Adhering Property | (Not Implemented) | | | ○ | ○ | ○ |
| | | Antistatic Property | X | X | X | X | X | X |
| | | Anti-fogging Property | ○ | ○ | ○ | ○ | ○ | ○ |
| | | Contact Angle | 17.1 | 9 | 10.1 | 11.1 | 12.4 | 19.3 |
| | After Aging Test | Surface Property | (Not Implemented) | | | | | |
| | | Adhering Property | | | | | | |
| | | Antistatic property | | | | | | |
| | | Variation of Surface Electric Resistance | | | | | | |
| | | Anti-fogging Property | | | | | | |
| | | Contact Angle | | | | | | |

S-3-1 Surfactant manufactured by Sino-Japan Chemical Co., LTD. and the trade name is 1105SF
S-3-2 Surfactant manufactured by Sino-Japan Chemical Co., LTD. and the trade name is 707SFI

TABLE 3

| | | | Example 2-1 | Example 2-2 | Example 2-3 | Example 2-4 | Example 2-5 | Example 2-6 | Example 2-7 | Example 2-8 | Example 2-9 | Example 2-10 | Example 2-11 | Example 2-12 |
|---|---|---|---|---|---|---|---|---|---|---|---|---|---|---|
| Composition (parts by weight) | Photo-curing Resin | R-1 | 100 | 100 | 100 | 100 | 100 | 100 | | | | | | |
| | | R-2 | | | | | | | 100 | 100 | 100 | 100 | 100 | 100 |
| | Surfactant | S-1-1 | | | | | | | | | | | | |
| | | S-1-2 | | | | | | | | | | | | |
| | | S-1-3 | | | | | | | | | | | | |
| | | S-2-1 | 0.5 | | | | | | 0.5 | | | | | |
| | | S-2-2 | | 0.5 | | | | | | 0.5 | | | | |
| | | S-2-3 | | | 0.5 | | | | | | 0.5 | | | |
| | | S-2-4 | | | | 0.5 | | | | | | 0.5 | | |
| | | S-2-5 | | | | | 0.5 | | | | | | 0.5 | |
| | | S-2-6 | | | | | | 0.5 | | | | | | 0.5 |
| | | S-3-1 | | | | | | | | | | | | |
| | | S-3-2 | | | | | | | | | | | | |
| Evaluation Method | Before Aging Test | Surface Property | ○ | ○ | ○ | ○ | ○ | ○ | ○ | ○ | ○ | ○ | ○ | ○ |
| | | Adhering Property | ○ | ○ | ○ | ○ | ○ | ○ | ○ | ○ | ○ | ○ | ○ | ○ |
| | | Antistatic Property | ○ | △ | ◎ | ○ | ◎ | ◎ | ○ | ○ | ◎ | ◎ | ◎ | ○ |
| | | Anti-fogging Property | ○ | ○ | ○ | ○ | ○ | △ | ○ | ○ | ○ | ○ | ○ | ○ |
| | | Contact Angle | 25.8 | 18.2 | 6.7 | 7.5 | 17.6 | 40.2 | 12.8 | 9 | 17.1 | 6.9 | 16.6 | 16.8 |
| | After Aging Test | Surface Property | ○ | ○ | ○ | ○ | ○ | ○ | ○ | ○ | ○ | ○ | ○ | ○ |
| | | Adhering Property | ○ | ○ | ○ | ○ | ○ | ○ | ○ | ○ | ○ | ○ | ○ | △ |
| | | Antistatic Property | △ | △ | △ | ○ | ○ | △ | △ | ○ | △ | ◎ | ◎ | ○ |
| | | Variation of Surface Electric Resistance | ○ | ○ | △ | ○ | ○ | ○ | ○ | ○ | △ | ○ | ○ | ○ |
| | | Anti-fogging Property | ○ | ○ | ○ | ○ | ○ | △ | ○ | ○ | △ | ○ | ○ | ○ |
| | | Contact Angle | 27.5 | 22.3 | 7.4 | 8 | 20 | 47 | 133 | 9.6 | 31.7 | 8 | 18.4 | 21.4 |

S-3-1 Surfactant manufactured by Sino-Japan Chemical Co., LTD. and the trade name is 1105SF
S-3-2 Surfactant manufactured by Sino-Japan Chemical Co., LTD. and the trade name is 707SFI

TABLE 4

| | | | Comparative Example 1 | Comparative Example 2 | Comparative Example 3 | Comparative Example 4 | Comparative Example 5 | Comparative Example 6 |
|---|---|---|---|---|---|---|---|---|
| Composition (parts by weight) | Photo-curing Resin | R-1 | 100 | 100 | 100 | | | |
| | | R-2 | | | | 100 | 100 | 100 |
| | Surfactant | S-1-1 | | | | | | |
| | | S-1-2 | | | | | | |
| | | S-1-3 | | | | | | |
| | | S-2-1 | | | | | | |
| | | S-2-2 | | | | | | |
| | | S-2-3 | | | | | | |
| | | S-2-4 | | | | | | |
| | | S-2-5 | | | | | | |
| | | S-2-6 | | | | | | |
| | | S-3-1 | | 0.5 | | | 0.5 | |
| | | S-3-2 | | | 0.5 | | | 0.5 |
| Evaluation Method | Before Aging Test | Surface Property | ○ | ○ | ○ | ○ | ○ | ○ |
| | | Adhering Property | ○ | ○ | ○ | ○ | ○ | ○ |
| | | Antistatic Property | X | ◎ | X | △ | ◎ | X |
| | | Anti-fogging Property | X | ○ | △ | X | ○ | △ |
| | | Contact Angle | 74.4 | 6.9 | 32.5 | 74.7 | 6.4 | 30.2 |

TABLE 4-continued

|  |  | Comparative Example 1 | Comparative Example 2 | Comparative Example 3 | Comparative Example 4 | Comparative Example 5 | Comparative Example 6 |
|---|---|---|---|---|---|---|---|
| After Aging Test | Surface Property | ○ | X | ○ | ○ | X | ○ |
|  | Adhering Property | ○ | (Cannot be Implemented) | ○ | ○ | (Cannot be Implemented) | ○ |
|  | Antistatic Property | X |  | X | Δ |  | X |
|  | Variation of Surface Electric Resistance | (Not Implemented) |  | (Not Implemented) | ○ |  | (Not Implemented) |
|  | Anti-fogging Property | X |  | X | X |  | X |
|  | Contact Angle | (Not Implemented) |  | (Not Implemented) |  |  | (Not Implemented) |

S-3-1 Surfactant manufactured by Sino-Japan Chemical Co., LTD. and the trade name is 1105SF
S-3-2 Surfactant manufactured by Sino-Japan Chemical Co., LTD. and the trade name is 7078FI

What is claimed is:

1. A composite film, comprising:
a substrate; and
a photo-curing film, disposed on a surface of the substrate, and the photo-curing film comprises a reaction product of a photo-curing resin and an alkoxylene derivative having a structure of following formula (VII), wherein a contact angle of the photo-curing film relative to water is not larger than 30 degrees, and based on an amount of the photo-curing resin as 100 parts by weight, an amount of the alkoxylene derivative is 0.2 to 15 parts by weight:

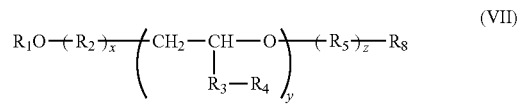

(VII)

in the formula (VII), $R_1$ represents an alkyl group of 8 to 30 carbons; $R_2$ represents an alkoxylene group of 2 to 4 carbons, and the alkylene group in $R_2$ is bonded with $R_1O$—; $R_3$ represents

(I)

wherein C═O is bonded with $R_4$, and r represents 0 or $R_4$ represents a functional group containing a C═C unsaturated group; $R_5$ represents an alkoxylene group of 2 to 4 carbons, and an oxygen atom of the terminal group in $R_5$ is bonded with $R_8$; $R_8$ represents a hydrogen atom or an anionic group, wherein the anionic group is selected from a group consisting of —$SO_3M$, —$PO_3M_2$, —$PO_3MH$, —COOM and a combination thereof, and M represents a hydrogen atom, an alkali metal atom, (an alkaline earth atom)$_{1/2}$, an ammonium group, an alkyl ammonium, or a alkanolammonium compound with or without an alkyl substituent; x represents an integer of 0 to 100; y represents an integer of 1 to 10; and z represents an integer of 1 to 100;
wherein the C═C unsaturated group in $R_4$ of the formula (VII) is bonded with the photo-curing resin.

2. The composite film of claim 1, wherein a first surface electric resistance of the composite film is less than $10^{11}$ ohm/(per unit area).

3. The composite film of claim 2, while the composite film is placed in an environment at 65° C. with humidity of 95%, a second surface electric resistance of the composite film is less than $10^{11}$ ohm/(per unit area), and a ratio of the second surface electric resistance to the first surface electric resistance is less than 100 and larger than 0.

4. The composite film of claim 3, wherein the ratio of the second surface electric resistance to the first surface electric resistance is less than 20 and larger than 0.

5. The composite film of claim 3, wherein the ratio of the second surface electric resistance to the first surface electric resistance is less than or equal to 16 and larger than 0.

* * * * *